United States Patent
He

(10) Patent No.: US 6,284,759 B1
(45) Date of Patent: Sep. 4, 2001

(54) 2-PIPERAZINOALKYLAMINOBENZO-AZOLE DERIVATIVES: DOPAMINE RECEPTOR SUBTYPE SPECIFIC LIGANDS

(75) Inventor: Xiao Shu He, Branford, CT (US)

(73) Assignee: Neurogen Corporation, Branford, CT (US)

(*) Notice: Subject to any disclaimer, the term of this patent is extended or adjusted under 35 U.S.C. 154(b) by 0 days.

(21) Appl. No.: 09/408,644

(22) Filed: Sep. 30, 1999

Related U.S. Application Data
(60) Provisional application No. 60/102,538, filed on Sep. 30, 1998.

(51) Int. Cl.$^7$ .................. A61K 31/496; C07D 401/14; C07D 403/12

(52) U.S. Cl. .................. 514/252.19; 514/253.09; 514/254.06; 514/253.1; 514/254.02; 544/295; 544/364; 544/370; 544/368; 544/373

(58) Field of Search .................. 544/370, 364, 544/253.09, 254.06, 295; 514/252.19

(56) References Cited

U.S. PATENT DOCUMENTS

| | | | |
|---|---|---|---|
| 2,863,752 | 12/1958 | Hamm et al. | 71/2.3 |
| 2,909,523 | 10/1959 | Bach, Jr. et al. | 260/268 |
| 3,268,584 | 8/1966 | Olin | 260/562 |
| 5,159,083 | 10/1992 | Thurkauf et al. | 548/335.5 |
| 5,192,775 | 3/1993 | Malen et al. | 514/321 |
| 5,229,398 | 7/1993 | Malen et al. | 514/321 |
| 5,229,399 | 7/1993 | Malen et al. | 514/321 |
| 5,428,164 | 6/1995 | Thurkauf et al. | 544/295 |
| 5,632,898 | 5/1997 | Jung et al. | 210/656 |
| 5,681,954 | 10/1997 | Yamamoto et al. | 544/114 |
| 5,731,438 | * 3/1998 | Cook et al. | 544/368 |
| 5,905,152 | 5/1999 | Gala et al. | 544/295 |

FOREIGN PATENT DOCUMENTS

| | | |
|---|---|---|
| 20 61 515 | 6/1971 | (DE) . |
| 26 04 224 | 8/1977 | (DE) . |
| 0 186 310 | 7/1986 | (EP) . |
| 0 332 364 | 9/1989 | (EP) . |
| 1 065 801 | 4/1967 | (GB) . |
| 53 018540 | 2/1978 | (JP) . |
| WO 92 12134 | 7/1992 | (WO) . |
| WO 94 22839 | 10/1994 | (WO) . |
| WO 96 10018 | 4/1996 | (WO) . |
| WO 96 16040 | 5/1996 | (WO) . |
| WO 96 16057 | 5/1996 | (WO) . |
| WO 96 39403 | 12/1996 | (WO) . |
| WO 97 43271 | 11/1997 | (WO) . |
| WO 97 43279 | 11/1997 | (WO) . |
| WO 98 07703 | 2/1998 | (WO) . |
| WO 98 07710 | 2/1998 | (WO) . |
| WO 98 37064 | 8/1998 | (WO) . |
| WO 98 56786 | 12/1998 | (WO) . |
| WO 99 21848 | 5/1999 | (WO) . |
| WO 99 23092 | 5/1999 | (WO) . |

OTHER PUBLICATIONS

Vantol et al, *Nature*, vol. 350 p. 611 (1991).*

Aleshnikova, T.V., et al., "2–(R–Amino)Pyrrolines and Their Analogs: Tetrahydro–Pyridines and –Azepines. II. Synthesis and Properties of Choroacetyl and [(Dialkoxy) Phosphinothioyl)Thio]Acetyl Derivatives," *Journal of General Chemistry, USSR*, 59(2):242–251 (Feb. 1989).

Andrewes, C.H., et al., "Experimental Chemotherapy of Typhus. Anti–rickettsial action of p–sulphonamidobenzamidine and related compounds," *Proceedings of the Royal Society of London, GB*, The Royal Society, London, vol. 133, Dec. 1946, pp. 20–62.

Aquino, C.J., et al., "Discovery of 1,5–Benzodiazepines with Peripheral Cholecystokinin (CCK–A) Receptor Agonist Activity. 1. Optimization of the Agonist "Trigger"," *Journal of Medicinal Chemistry*, 39(2):562–569 (Jan. 19, 1996).

Barfield, M., et al., "Conformational, Bond–Order, and Substituent Dependencies of Orthobenzylic Coupling Constants," *J. Am. Chem. Soc.*, 105:2178–2186 (1983).

Boyfield, I., "Design and Synthesis of 2–Naphthonate Esters as Selective Dopamine $D_4$ Antagonists," *Journal of Medicinal Chemistry*, 39(10):1946–1948 (May 10, 1996).

Bradsher, C., et al., "Oxygen Heterocycles by the Parham Cyclialkylation," *J. Org. Chem.*, 46(7):1384–1388 (1981).

(List continued on next page.)

*Primary Examiner*—Emily Bernhardt
(74) *Attorney, Agent, or Firm*—McDonnell Boehnen Hulbert & Berghoff; Steven J. Sarussi

(57) ABSTRACT

Disclosed are compounds of the formula:

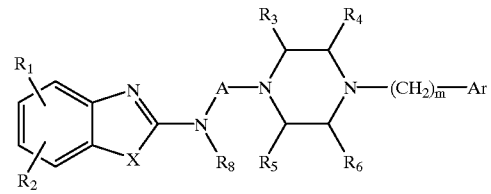

or pharmaceutically acceptable salts thereof, wherein:

A is (un)substituted alkylene;

$R_1$ and $R_2$ are the same or different and represent hydrogen, halogen, alkyl, alkoxy, alkylthio, hydroxy, (un)substitutedamino, cyano, nitro, sulfonamide, trifluoromethyl or trifluoromethoxy;

$R_3$, $R_4$, $R_5$, $R_6$, and $R_8$ are independently hydrogen or alkyl; and

X is sulfur, oxygen or $NR_7$ where $R_8$ is defined herein;

m is an integer chosen from 0, 1 or 2; and

Ar is an aryl or heteroaryl group as further defined herein, which compounds are useful for the treatment and/or prevention of neuropsychological disorders including, but not limited to, schizophrenia, mania, dementia, depression, anxiety, compulsive behavior, substance abuse, Parkinson-like motor disorders and motion disorders related to the use of neuroleptic agents.

19 Claims, No Drawings

OTHER PUBLICATIONS

Chupp, J., "Structural Factors Influencing Rotational Isomerism and Alkylation Properties in Some Alpha–Haloacetanilies," *The Journal of Organic Chemistry*, 34(5):1192–1197 (May 1969).

Clark, N.G., et al., "The Fungicidal Activity of Substituted Acetanilides and Related Compounds," *Biochemical Journal*, 55(5):839–851 (1953).

Diehl, K., et al., "Intramolekulare Diels–Alder–Reaktionen bei Allencarboxaniliden; Variation der Substituenten in p–Position des Anilinkerns," *Chemische Berichte*, 119(8):2430–2443 (1986).

Ferraro, J.J., et al., "Preparation of Some N–Substituted Halogeno–anilines and –anilides by an Improved N–Alkylation," *Journal of the Chemical Society*, 1964, pp. 2813–2816.

Grothe, V., "Ueber die Anilide von Alkylsulfonessigsäuren," *Archiv der Pharmazie*, 238(8):587–600 (1900).

Hadley, M.S., "$D_4$ Receptors and Their Antagonists," *Medicinal Research Reviews*, 16(6):507–526 (Jun. 1996).

He, X., et al., "A New Series of Selective Dopamine $D_4$ Ligands: 3–([4–Arylpiperazin–1–yl]Alkylamino)–2H–1, 4–Benzoxazines," *Bioorganic & Medicinal Chemistry Letters*, 7(18):2399–2402 (1997).

Henke, B.R., et al., "Optimization of 3–(1H–Indazol–3–ylmethyl)–1,5–benzodiazepines as Potent, Orally Active CCK–A Agonists," *Journal of Medicinal Chemistry*, 40(17):2706–2725 (Aug. 15, 1997).

Hromatka, O., et al., "Über das Hexahydrophenthiazin, 3. Mitt.," *Monatsheft der Chemie*, 92(1):88–95 (1961).

Kulagowski, J.J., et al., "Dopamine $D_4$ Receptor Antagonists," *Current Pharmaceutical Design*, 3(4):355–366 (1997).

Liégeois, J.F., et al., "Dopamine $D_4$ Receptors: A New Opportunity for Research on Schizophrenia," *Curr. Med. Chem.*, 5(2):77–100 (1998).

Matsumura, K., et al., "Studies of Nitriles. XI. Preparation and chemistry of Schiff bases of ADAN, 2–Amino–3, 3–dichloroacrylonitrile. A highly effective conversion into 2–substituted–4(5)–chloroimidazole–5(4)–carbaldehydes," *Chem. Pharm. Bull.*, 24:960–969 (1976).

Mukaiyama, T., et al., "Pyrolysis of Acid Amides. II. Pyrolysis of 2–Haloacetamides," *The Journal of Organic Chemistry*, 27(1–4):803–805 (1962).

Najer, H., et al., "N–phényl N–cyclohexyl carbamates tertioaminoalcoyle et N–phényl N–cyclohexyl tertioaminoacylamides," *Annales Pharmaceutiques Françaises*, 17:200–211 (1959).

Ohtaka, H., et al., "Benzylpiperazine Derivatives. VIII. Syntheses, Antiulcer and Cytoprotective Activities of 1–(Aminocarbonylalkyl)–4–benzylpiperazine Derivatives and Related Compounds," *Chemical & Pharmaceutical Bulletin*, 36(10):3948–3954 (Oct. 1988).

Siddall III, T.H., et al., "Geminal Proton Nonequivalences and Related Phenomena in Some N–Substituted Amides," *Journal of the American Chemical Society*, 88(6):1172–1176 (Mar. 1966).

Thurkauf, A., et al., "2–Phenyl–4(5)–[[4–(pyrimidin–2–yl)piperazin–1–yl]methyl]imidazole. A highly selective antagonist at cloned human $D_4$ receptors," *J. Med Chem.*, 40(1):1–3 (Jan. 3, 1997).

Thurkauf, A., et al., "2–Phenyl–4–(aminoethyl)imidazoles as Potential Antipsychotic Agents, Synthesis and Dopamine $D_2$ Receptor Binding," *J. Med. Chem.*, 38(12):2251–2255 (1995).

Wiseman, E., et al., "Studies with Antiinflammatory Oxindolecarboxanilides," *Journal of Medical Chemistry*, 16(2):131–134 (Feb. 1973).

* cited by examiner

2-PIPERAZINOALKYLAMINOBENZO-AZOLE DERIVATIVES: DOPAMINE RECEPTOR SUBTYPE SPECIFIC LIGANDS

This application claims benefit of U.S Provisional Application Ser. No. 60/102,538, filed Sep. 30, 1998.

BACKGROUND OF THE INVENTION

1. Field of the Invention

This invention relates to 2-piperazinoalkylaminobenzoazole derivatives and to pharmaceutical compositions containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified (Nature, 350: 610 (Van Tol et al., 1991); Nature, 347: 146 (Sokoloff et al., 1990)). Its unique localization in limbic brain areas and its differential recognition of various antipsychotics indicates that the $D_4$ receptor plays a major role in the etiology of schizophrenia. Selective $D_4$ antagonists are considered effective antipsychotics free from the neurological side effects displayed by conventional neuroleptics.

U.S. Pat. No. 5,632,898 discloses N-benzothiazol-2-yl-2-(4-phenylpiperazinyl)acetamide.

U.S. Pat. No. 5,229,398 discloses alminomethylpiperidine derivatives.

SUMMARY OF THE INVENTION

This invention provides novel compounds of Formula I which interact with dopamine subtypes. Accordingly, a broad embodiment of the invention is directed to a compound of Formula I:

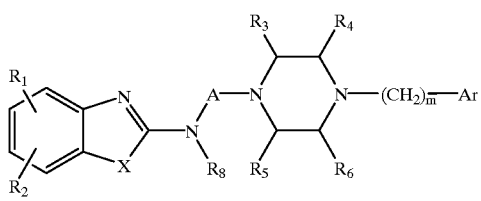

wherein

A is $C_1$–$C_6$ alkylene optionally substituted with one or two $C_1$–$C_6$ alkyl groups;

$R_1$ and $R_2$ are the same or different and represent hydrogen, halogen, $C_1$–$C_6$ alkyl, $C_1$–$C_6$ alkoxy, $C_1$–$C_6$ alkylthio, hydroxy, amino, mono- or di($C_1$–$C_6$)alkylamino, cyano, nitro, $C_1$–$C_6$ alkylsulfonyl, sulfonamide or $C_1$–$C_6$ alkyl sulfonamide, perfluoro($C_1$–$C_6$)alkyl or perfluoro($C_1$–$C_6$) alkoxy;

$R_3$, $R_4$, $R_5$, and $R_6$ are the same or different and represent hydrogen or $C_1$–$C_6$ alkyl;

X is sulfur, oxygen or $NR_7$ where $R_7$ is hydrogen or $C_1$–$C_6$ alkyl;

$R_8$ is hydrogen or $C_1$–$C_6$ alkyl;

m is 0 or an integer chosen from 1 and 2; and

Ar represents mono or bicyclic aryl or heteroaryl, each of which is optionally substituted independently with up to five groups selected from $C_1$–$C_6$ alkyl, $C_1$–$C_6$ alkoxy, halogen, $C_1$–$C_6$ alkylthio, hydroxy, amino, mono- or di($C_1$–$C_6$) alkylamino, cyano, nitro, trifluoromethyl, trifluoromethoxy, $C_1$–$C_6$ alkylsulfonyl, sulfonamide, or alkyl sulfonamide.

Dopamine $D_4$ receptors are concentrated in the limbic system (Science, 265: 1034 (Taubes, 1994)) which controls cognition and emotion. Therefore, compounds that interact with these receptors are useful in the treatment of cognitive disorders. Such disorders include cognitive deficits which are a significant component of the negative symptoms (social withdrawal and unresponsiveness) of schizophrenia. Other disorders include those involving memory impairment or attention deficit disorders.

Compounds of the present invention demonstrate high affinity and selectivity in binding to the $D_4$ receptor subtype. These compounds are therefore useful in treatment of a variety of neuropsychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Compounds of this invention are also useful in the treatment of depression, memory-impairment or Alzheimer's disease by modulation of $D_4$ receptors since they exist selectively in areas known to control emotion and cognitive functions.

Thus, in another aspect, the invention provides methods for treatment and/or prevention of neuropsychological or affective disorders including, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents. In addition, the compounds of the invention are useful in treatment of depression, memory-impairment or Alzheimer's disease. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

In yet another aspect, the invention provides pharmaceutical compositions comprising compounds of Formula I.

In another aspect, the invention provides intermediates useful in the preparation of compounds of Formula I.

DETAILED DESCRIPTION OF THE INVENTION

As mentioned above, the invention relates to compounds of Formula I. Preferred compounds of Formula I include those where $R_3$, $R_4$, $R_5$, and $R_6$ independently represent hydrogen or methyl; and $R_8$ is hydrogen. In more preferred compounds of I, m is 0 or 1; and A is unsubstituted $C_1$–$C_4$, more preferably unsubstituted $C_2$, $C_3$, or $C_4$, alkylene. In preferred compounds of Formula I, Ar is not unsubstituted phenyl when X is S, $R_1$ and $R_2$ are both hydrogen, all of $R_2$–$R_6$ are hydrogen, and m is 0.

Preferred Ar groups in Formula I are those having up to three non-hydrogen substituents selected from the group mentioned above. More preferred Ar groups in Formula I are those having no more than two substituents. Particularly preferred compounds of Formula I include those where Ar is selected from

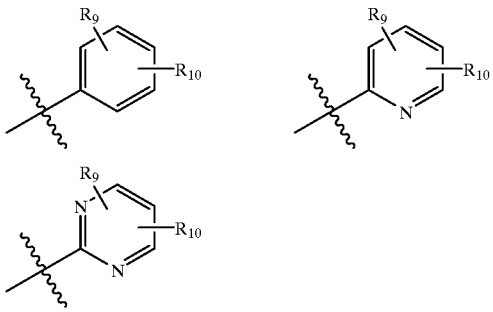

where each of $R_9$ and $R_{10}$ is independently selected from hydrogen, $C_1$–$C_6$ alkyl, $C_1$–$C_6$ alkoxy, halogen, or trifluoromethyl.

In other particularly preferred compounds of I, $R_9$ and $R_{10}$ are independently selected from hydrogen, $C_1$–$C_3$ alkyl, $C_1$–$C_3$ alkoxy, chloro or fluoro, or trifluoromethyl. In yet other highly preferred compounds of Formula I, Ar is

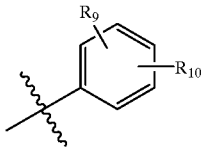

here each of $R_9$ and $R_{10}$ is independently selected from ydrogen, 4-$C_1$–$C_3$ alkyl, 2-$C_1$–$C_3$ alkoxy, 4-halogen, or 3-trifluoromethyl, provided that one of $R_9$ and $R_{10}$ is hydrogen. Even more preferred are compounds where $R_9$ and $R_{10}$ are independently selected from hydrogen, methyl, methoxy, ethoxy, isopropoxy, chloro, or fluoro.

In another group of preferred compounds of Formula I, R, and $R_2$ independently represent hydrogen, halogen, $C_1$–$C_6$ alkoxy, $C_1$–$C_6$ alkyl, $C_1$–$C_6$ alkylsulfonyl, alkyl sulfonamide, or sulfonamide. A highly preferred group of such compounds include those where at least one of $R_1$ and $R_2$ is hydrogen and the other is methoxy, methyl, chloro, fluoro, methoxy, ethoxy, or methylsulfonyl. Particularly preferred compounds of this group include those where $R_1$ is hydrogen and $R_2$ is in the 4 or 6 position on the nitrogen containing ring system.

In still another group of preferred compounds of Formula I, Ar is a naphthyl group of the formula

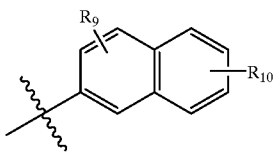

where each of $R_9$ and $R_{10}$ is independently selected from hydrogen, $C_1$–$C_6$ alkyl, $C_1$–$C_6$ alkoxy, halogen, or trifluoromethyl. A preferred group of compounds having the above naphthyl and where X is NH.

A preferred group of compounds of the invention is represented by Formula II:

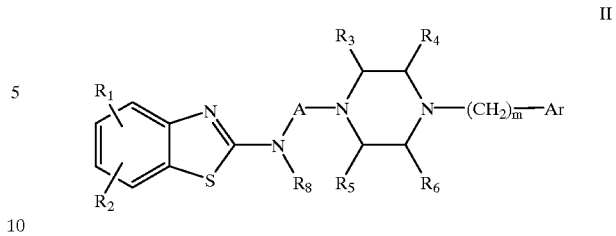

wherein

A is $C_2$–$C_6$ alkylene optionally substituted with one or two $C_1$–$C_6$ alkyl groups;

$R_1$ and $R_2$ are as defined above for Formula I;

$R_3$, $R_4$, $R_5$, and $R_6$ independently represent hydrogen or $C_1$–$C_3$ alkyl, preferably methyl;

$R_8$ is hydrogen or $C_1$–$C_2$ alkyl;

m is an integer chosen from 0, 1 or 2; and

Ar is as defined above for Formula I.

In more preferred compounds of II, m is 0 or 1; and A is unsubstituted $C_1$–$C_4$ more preferably unsubstituted $C_2$, $C_3$, or $C_4$, alkylene.

Particularly preferred compounds of Formula II include those where Ar is selected from

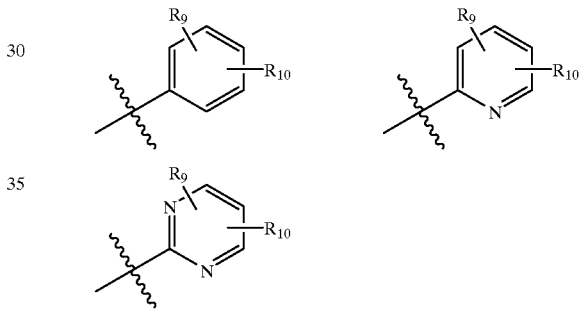

where each of $R_9$ and $R_{10}$ is independently selected from hydrogen, $C_1$–$C_6$ alkyl, $C_1$–$C_6$ alkoxy, halogen, or trifluoromethyl. In highly preferred such compounds, not both $R_9$ and $R_{10}$ are hydrogen when Ar is phenyl, $R_1$–$R_6$ are hydrogen, m is 0, and A is ethylene. In other highly preferred compounds of Formula II, Ar is selected from pyridyl and pyrimidinyl groups of the formula:

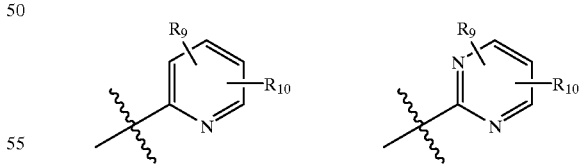

where each of $R_9$ and $R_{10}$ is independently selected from hydrogen, $C_1$–$C_6$ alkyl, $C_1$–$C_6$ alkoxy, halogen, or trifluoromethyl.

In other particularly preferred compounds of II, $R_9$ and $R_{10}$ are independently selected from hydrogen, $C_1$–$C_3$ alkyl, $C_1$–$C_3$ alkoxy, chloro or fluoro, or trifluoromethyl, provided not both $R_9$ and $R_{10}$ are hydrogen when Ar is phenyl, $R_1$–$R_6$ are hydrogen, A is ethylene, and m is 0. In yet other highly preferred compounds of Formula II, Ar is

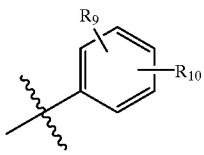

where each of $R_9$ and $R_{10}$ is independently selected from hydrogen, 4-$C_1$–$C_3$ alkyl, 2-$C_1$–$C_3$ alkoxy, 4-halogen, or 3-trifluoromethyl, provided that only one of $R_9$ and $R_{10}$ is hydrogen. Even more preferred are compounds where $R_9$ and $R_{10}$ are independently selected from hydrogen, methyl, methoxy, ethoxy, isopropoxy, chloro, or fluoro with the proviso that when $R_1$–$R_6$ are hydrogen, A is ethylene, m is 0, and Ar is phenyl, not both $R_9$ and $R_{10}$ are hydrogen.

In another group of preferred compounds of Formula II, $R_1$ and $R_2$ independently represent hydrogen, halogen, $C_1$–$C_6$ alkoxy, $C_1$–$C_6$ alkyl, $C_1$–$C_6$ alkylsulfonyl, alkyl sulfonamide or sulfonamide. A highly preferred group of such compounds include those where at least one of $R_1$ and $R_2$ is hydrogen and the other is methoxy, methyl, chloro, fluoro, methoxy, ethoxy, or methylsulfonyl. Particularly preferred compounds of this group include those where $R_1$ is hydrogen and $R_2$ is in the 4 or 6 position on the nitrogen containing ring system.

In still another group of preferred compounds of Formula II, Ar is a naphthyl group of the formula

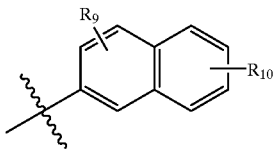

where each of $R_9$ and $R_{10}$ is independently selected from hydrogen, $C_1$–$C_6$ alkyl, $C_1$–$C_6$ alkoxy, halogen, or trifluoromethyl. A preferred group of compounds are those having the above naphthyl where X is NH.

Another preferred group of compounds of the invention is represented by Formula III:

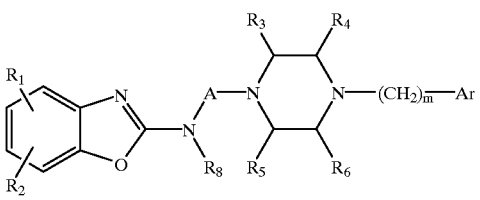

III wherein:
A is $C_2$–$C_6$ alkylene optionally substituted with one or two $C_1$–$C_6$ alkyl groups;
$R_1$ and $R_2$ are as defined above for Formula I;
$R_3$, $R_4$, $R_5$, and $R_6$ independently represent hydrogen or $C_1$–$C_3$ alkyl, preferably methyl;
$R_8$ is hydrogen or $C_1$–$C_2$ alkyl;
m is an integer chosen from 0, 1 or 2; and
Ar is as defined above for Formula I.

In more preferred compounds of III, m is 0 or 1; and A is unsubstituted $C_1$–$C_4$, more preferably unsubstituted $C_2$, $C_3$, or $C_4$, alkylene.

Particularly preferred compounds of Formula III include those where Ar is selected from

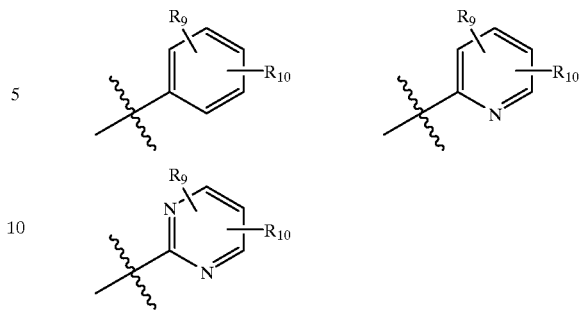

where each of $R_9$ and $R_{10}$ is independently selected from hydrogen, $C_1$–$C_6$ alkyl, $C_1$–$C_6$ alkoxy, halogen, or trifluoromethyl.

In other particularly preferred compounds of III, $R_9$ and $R_{10}$ are independently selected from hydrogen, $C_1$–$C_3$ alkyl, $C_1$–$C_3$ alkoxy, chloro or fluoro, or trifluoromethyl.

In highly preferred compounds of Formula III, Ar is selected from pyridyl and pyrimidinyl groups of the formula:

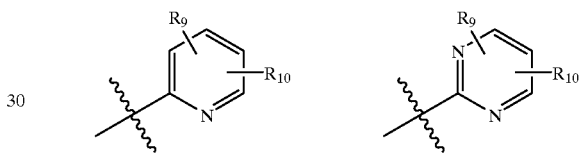

where each of $R_9$ and $R_{10}$ is independently selected from hydrogen, $C_1$–$C_6$ alkyl, $C_1$–$C_6$ alkoxy, halogen, or trifluoromethyl.

In Iyet other highly preferred compounds of Formula III, Ar is

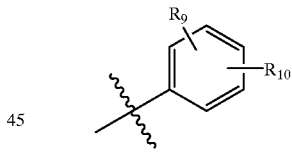

where each of $R_9$ and $R_{10}$ is independently selected from hydrogen, 4-$C_1$–$C_3$ alkyl, 2-$C_1$–$C_3$ alkoxy, 4-halogen, or 3-trifluoromethyl, provided that one of $R_9$ and $R_{10}$ is hydrogen. Even more preferred are compounds where $R_9$ and $R_{10}$ are independently selected from hydrogen, methyl, methyoxy, ethoxy, isopropoxy, chloro, or fluoro.

In another group of preferred compounds of Formula III, $R_1$ and $R_2$ independently represent hydrogen, halogen, $C_1$–$C_6$ alkoxy, $C_1$–$C_6$ alkyl, $C_1$–$C_6$ alkylsulfonyl, sulfonamide, or alkyl sulfonamide. A highly preferred group of such compounds include those where at least one of $R_1$ and $R_2$ is hydrogen and the other is methoxy, methyl, chloro, fluoro, methoxy, ethoxy, or methylsulfonyl. Particularly preferred compounds of this group include those where $R_1$ is hydrogen and $R_2$ is in the 4 or 6 position on the nitrogen containing ring system.

In still another group of preferred compounds of Formula III, Ar is a naphthyl group of the formula

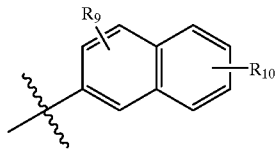

where each of $R_9$ and $R_{10}$ is independently selected from hydrogen, $C_1$–$C_6$ alkyl, $C_1$–$C_6$ alkoxy, halogen, or trifluoromethyl. A preferred group of compounds having the above naphthyl and where X is NH.

Yet another preferred group of compounds of the invention is represented by Formula IV:

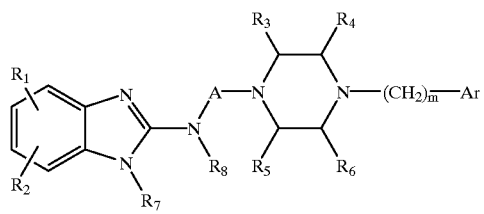

wherein:

A is $C_2$–$C_6$ alkylene optionally substituted with one or two $C_1$–$C_6$ alkyl groups;
$R_1$ and $R_2$ are as defined above for Formula I;
$R_3$, $R_4$, $R_5$, and $R_6$ independently represent hydrogen or $C_1$–$C_3$ alkyl, preferably methyl;
$R_7$ is hydrogen or $C_1$–$C_3$ alkyl;
$R_8$ is hydrogen or $C_1$–$C_2$ alkyl;
m is an integer chosen from 0, 1 or 2; and
Ar is as defined above for Formula I.

In more preferred compounds of III, m is 0 or 1; and A is unsubstituted $C_1$–$C_4$, more preferably unsubstituted $C_2$, $C_3$, or $C_4$, alkylene.

Particularly preferred compounds of Formula III include those where Ar is selected from

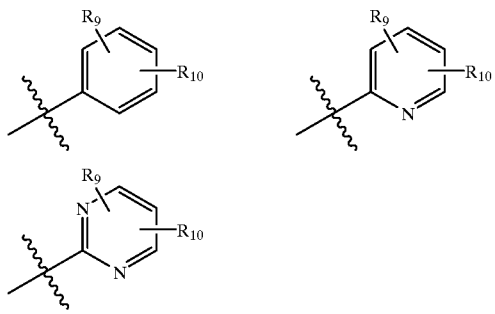

where each of $R_9$ and $R_{10}$ is independently selected from hydrogen, $C_1$–$C_6$ alkyl, $C_1$–$C_6$ alkoxy, halogen, or trifluoromethyl.

In other particularly preferred compounds of III, $R_9$ and $R_{10}$ are independently selected from hydrogen, $C_1$–$C_3$ alkyl, $C_1$–$C_3$ alkoxy, chloro or fluoro, or trifluoromethyl. In yet other highly preferred compounds of Formula III, Ar is

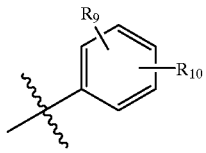

where each of $R_9$ and $R_{10}$ is independently selected from hydrogen, 4-$C_1$–$C_3$ alkyl, 2-$C_1$–$C_3$ alkoxy, 4-halogen, or 3-trifluoromethyl, provided that one of $R_9$ and $R_{10}$ is not hydrogen. Even more preferred are compounds where $R_9$ and $R_{10}$ are independently selected from hydrogen, methyl, methyoxy, ethoxy, isopropoxy, chloro, or fluoro.

In another group of preferred compounds of Formula III, $R_1$ and $R_2$ independently represent hydrogen, halogen, $C_1$–$C_6$ alkoxy, $C_1$–$C_6$ alkyl, $C_1$–$C_6$ alkylsulfonyl, sulfonamide, or alkyl sulfonamide. A highly preferred group of such compounds include those where at least one of $R_1$ and $R_2$ is hydrogen and the other is methoxy, methyl, chloro, fluoro, methoxy, ethoxy, or methylsulfonyl. Particularly preferred compounds of this group include those where $R_1$ is hydrogen and $R_2$ is a non-hydrogen group as specified immediately above and is in the 4 or 6 position on the nitrogen containing ring system.

In still another group of preferred compounds of Formula III, Ar is a naphthyl group of the formula

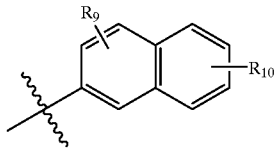

where each of $R_9$ and $R_{10}$ is independently selected from hydrogen, $C_1$–$C_6$ alkyl, $C_1$–$C_6$ alkoxy, halogen, or trifluoromethyl. A preferred group of compounds having the above naphthyl and where X is NH.

The invention also provides intermediates useful in preparing compounds of Formula I. These intermediates have Formulae VIII.

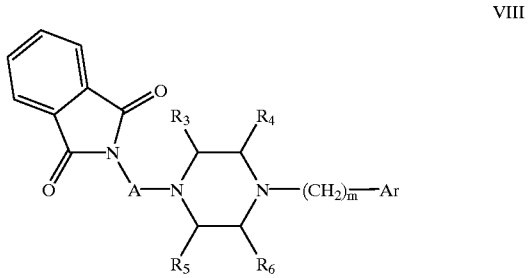

In Formula VIII, $R_3$, $R_4$, $R_5$, $R_6$, A, m and Ar are as defined above for Formula I.

In preferred compounds of VIII, m is 0 or 1; and A is unsubstituted $C_1$–$C_4$, more preferably unsubstituted $C_2$, $C_3$, or $C_4$, alkylene.

Particularly preferred compounds of Formula VIII include those where Ar is selected from

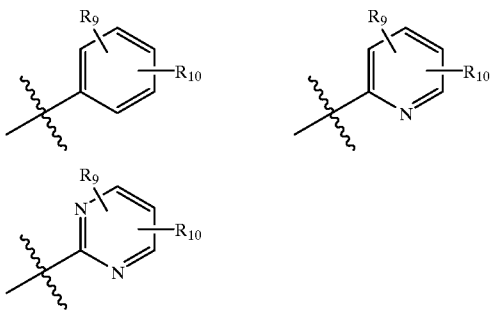

where each of $R_9$ and $R_{10}$ is independently selected from hydrogen, $C_1$–$C_6$ alkyl, $C_1$–$C_6$ alkoxy, halogen, or trifluoromethyl.

In other particularly preferred compounds of VIII, $R_9$ and $R_{10}$ are independently selected from hydrogen, $C_1$–$C_3$ alkyl, $C_1$–$C_3$ alkoxy, chloro or fluoro, or trifluoromethyl. In yet other highly preferred compounds of Formula VIII, Ar is

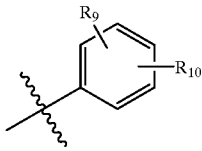

where each of $R_9$ and $R_{10}$ is independently selected from hydrogen, 4-$C_1$–$C_3$ alkyl, 2-$C_1$–$C_3$ alkoxy, 4-halogen, or 3-trifluoromethyl. Even more preferred are compounds where $R_9$ and $R_{10}$ are independently selected from hydrogen, methyl, methyoxy, ethoxy, isopropoxy, chloro, or fluoro.

In still another group of preferred compounds of Formula VIII, Ar is a naphthyl group of the formula

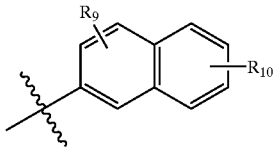

where each of $R_9$ and $R_{10}$ is independently selected from hydrogen, $C_1$–$C_6$ alkyl, $C_1$–$C_6$ alkoxy, halogen, or trifluoromethyl.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table 1 and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)$_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautomers. The invention includes all tautomeric forms of a compound.

By "$C_1$–$C_6$ alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, butyl, cyclopropyl and cyclopropylmethyl.

By "$C_1$–$C_6$ alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. Preferred alkoxy groups herein are $C_1$–$C_4$ alkoxy groups.

By the term "halogen" in the present invention is meant fluorine, bromine, chlorine, and iodine.

Where a substituent is a di($C_1$–$C_6$)alkylamino group, the two alkyl groups are the same or different. Representative di ($C_1$–$C_6$) alkylamino groups include dimethylamino, methylpropylamino, diisopropylamino, and ethylpentylamino.

By aryl is meant an aromatic carbocyclic group having one ring (e.g., phenyl), or two rings (e.g., biphenyl). Such groups are unsubstituted or substituted with up to five groups elected from $C_1$–$C_6$ alkyl, $C_1$–$C_6$ alkoxy, halogen, $C_1$–$C_6$ alkylthio, hydroxy, amino, mono- or di($C_1$–$C_6$) alkylamino, cyano, nitro, trifluoromethyl, trifluoromethoxy, $C_1$–$C_6$ alkylsulfonyl, alkyl sulfonamide and sulfonamide.

By heteroaryl (aromatic heterocycle) in the present invention is meant one or more aromatic ring systems of 5-, 6-, or 7-membered, preferably 5- or 6-membered, rings containing at least one and up to four, preferably one or two, hetero atoms selected from nitrogen, oxygen, or sulfur. The heteroaryl Ar groups are bound to the parent alkylpiperazine moiety through a carbon atom in the heteroaryl group, preferably a carbon atom immediately adjacent a hetero atom such as nitrogen. Such heteroaryl groups include, for example, thienyl, furanyl, thiazolyl, imidazolyl, (is) oxazolyl, pyridyl, pyrimidinyl, (iso)quinolinyl, naphthyridinyl, benzimidazolyl, and benzoxazolyl.

By "$C_1$–$C_6$ alkyl sulfonyl" is meant groups of the formula:

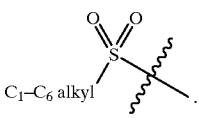

By the terms "$C_1$–$C_6$ alkyl sulfonamide" and "alkyl sulfonamide" is meant groups of the formula:

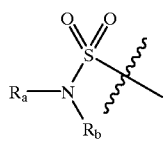

where $R_a$ and $R_b$ independently represent $C_1$–$C_6$ alkyl. Preferred $C_1$–$C_6$ alkyl sulfonamides are methylsulfonamide, dimethylsulfonamide, and diethylsulfonamide.

By the term "sulfonamide" is meant groups of the formula:

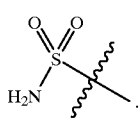

The convention for numbering the substituents about the nitrogen containing ring system herein is as follows:

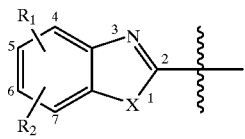

Representative compounds of the invention are shown in Table 1.

TABLE 1

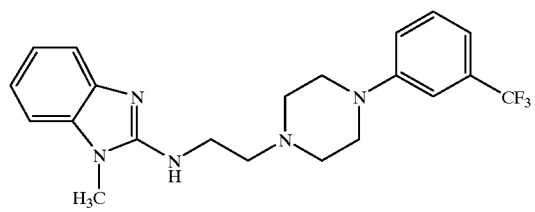

Compound 1

Compound 2

TABLE 1-continued

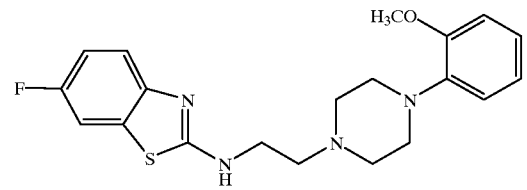

Compound 3

Compound 4

Compound 5

Compound 6

Compound 7

Compound 8

TABLE 1-continued

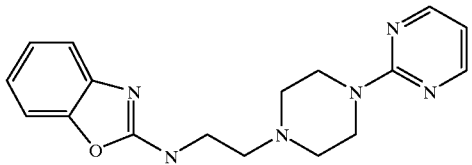

Compound 9

The invention also pertains to the use of compounds of general Formula I in the treatment of neuropsychological disorders. The interaction of compounds of the invention with dopamine receptors is shown in the examples. This interaction results in the pharmacological activity of these compounds.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative synthesis of the compounds of the invention is presented in Scheme I. Those having skill in the art will recognize that the starting materials may be varied and additional steps employed to produce compounds encompassed by the present invention.

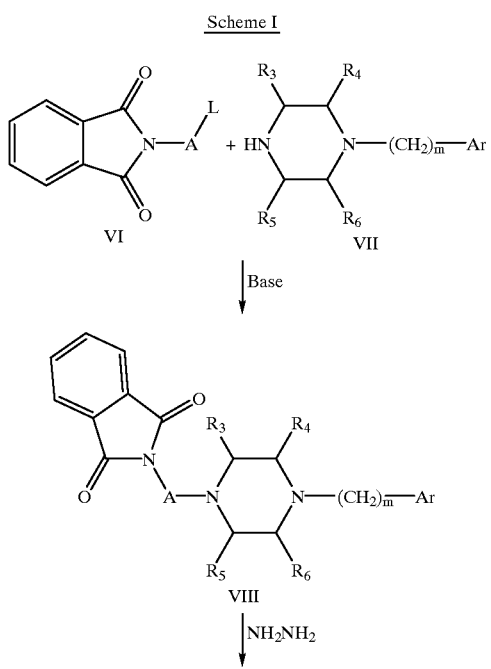

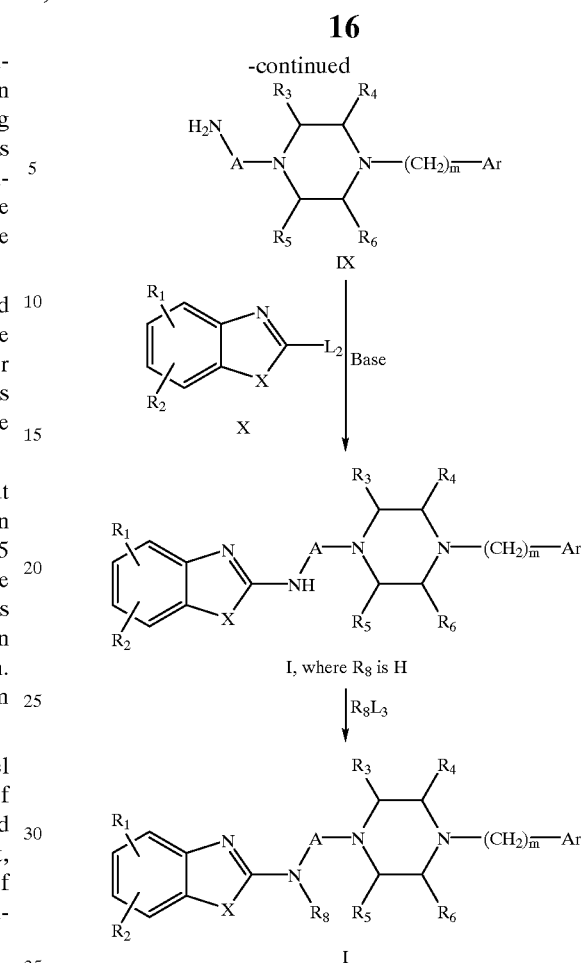

wherein $R_1$, $R_2$, $R_3$, $R_4$, $R_5$, $R_6$, $R_8$, X, m and Ar are as defined above for Formula I. $L_1$, $L_2$ and $L_3$ represent leaving groups as discussed below.

As shown in Scheme I, an N-alkylphthalimide VI substituted with an appropriate leaving group L may be reacted with an appropriately substituted piperazine VII in the presence of a base to afford N-(piperazinylalkyl)phthalimide VIII. The leaving group L on VI may be a halogen, a trialkylamino group, a sulphonate ester, or the like. Any suitable base can be employed; representative bases include inorganic bases such as sodium hydroxide, potassium carbonate or the like, and organic bases such as a triethylamine, pyridine or the like.

Phthalimide VIII may be treated with hydrazine or the like to afford amine IX. Amine IX may then be reacted with an appropriately substituted compound of Formula X having a leaving group $L_2$ at the 2-position to afford compounds of Formula I. The leaving group $L_2$ on alkylating agent X may be a halide, sulphonate ester or the like. Conversion of I where $R_8$ is hydrogen to compounds of I where $R_8$ is alkyl may be achieved by treating I with an appropriately alkyl halide, $R_8L_3$.

Where they are not commercially available, the compounds of general structure VI, VII and X may be prepared by procedures analogous to those described in literature. The compounds of general structure VI, VII, and X are either known or capable of being prepared by the methods known in the art. Those having skill in the art will recognize that the starting material may be varied and additional steps employed to produce compounds encompassed by the present invention. The base employed may be an inorganic base such as potassium carbonate, sodium hydroxide or the like; or an organic base such as triethylamine, pyridine or the like.

Alternatively, a compound of Formula X where $L_2$ is $NH_2$ may be sequentially reacted with chloroacetyl chloride and a compound of general structure VII in the presence of base followed by reduction to provide a compound of Formula I wherein A is ethylene.

EXAMPLE 1

1-(5-Fluoropyrimidin-2-yl)-4-(4-aminobutyl) piperazine

A solution of 4-bromo-N-butylphthalimide (8.37 g) and 1-(5-fluoropyrimidin-2-yl)piperazine (5.4 g) in dimethylformamide (100 mL) containing potassium carbonate (8.2 g) is stirred at 80° C. for 12 hours. After cooling, the mixture is poured into water and extracted with ether. The ether layer is dried over sodium sulfate, filtered and concentrated to give the intermediate as a yellow solid. The resulting phthalamide is then taken up in hydrazine monohydrate (100 ml) and refluxed under nitrogen overnight. After cooling, the mixture is poured into a 30% solution of potassium carbonate (500 ml), and extracted with methylene chloride, dried and concentrated to give an orange semisolid (4.66 g). This material is dissolve in a mixture of 10% methanol/isopropanol (50 ml), treated with fumaric acid (4.27 g, 2 eq) and the solvent volume reduced to 20 ml. The resulting yellow crystals are collected by filtration (6.5 g).

EXAMPLE 2

1-(5-Fluoropyrimidin-2-yl)-4-(2-[6-benzothiazol-2-ylamino]butyl) piperazine difumarate

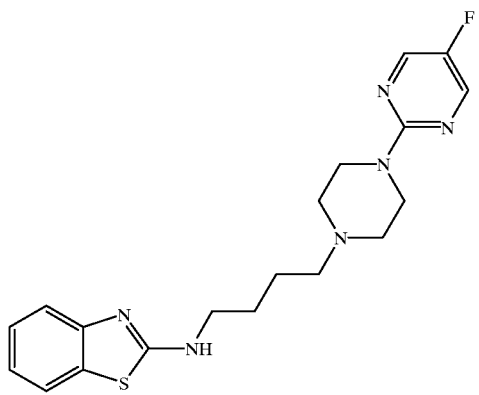

A solution of 2-chlorobenzothiazole (920 mg) and 1-(5-Fluoropyrimidin-2-yl)-4-(4-aminobutyl)piperazine (254 mg) in acetonitrile (10 mL) containing potassium carbonate (300 mg) is refluxed under nitrogen for 10 hours. After cooling, the mixture is concentrated, and the resulting residue partitioned between ethyl acetate and water. The organic layer is separated and extracted with 10% citric acid. The acidic aqueous layer is basified with 10 N NaOH solution and extracted with chloroform. The chloroform layer is then dried over sodium sulfate, filtered and concentrated to give a white solid (0.31 g) to provide the title compound. [alternatively named benzothiazol-2-yl{4-[4-(5-fluoropyrimidin-2-yl)piperazinyl]butyl}amine]. This material is dissolved in 10% methanol/isopropanol and treated with fumaric acid (190 mg). The volume of solvent is partially reduced and the resulting crystals are isolated by filtration (347 mg, m.p. 168–170° C.).

EXAMPLE 3

1-(2-Methoxyphenol)-4-(2-[6-fluorobenzothiazol-2-ylamino]ethyl) piperazine difumarate

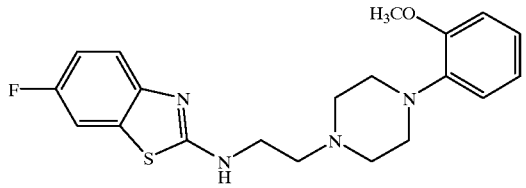

A solution of 6-fluoro-2-aminobenzothiazole (5 g) and triethylamine (5 ml) in chloroform (100 ml) is vigorously stirred during the dropwise addition of a solution of chloroacetyl chloride (5 ml) in chloroform (10 ml). The reaction mixture is stirred overnight, filtered and concentrated. The residue is triturated with isopropanol to give an off white solid (3.82 g).

A portion of this solid (150 mg, 0.61 mmol) was dissolved in acetonitrile (10 ml) and to the resulting solution is added 1-(2-methoxyphenyl)piperazine (118 mg) and potassium carbonate (150 mg). The mixture is refluxed overnight. After cooling, the solvent is removed and the resulting residue partitioned between ethyl acetate and water. The organic layer is dried and evaporated to provide a yellow oil which is purified by preparative thin layer chromatography eluting with 9% methanol/chloroform.

The product isolated after chromatography is dissolved in tetrahydrofuran (5 ml) and the resulting solution combined with a 1 M solution of alane in tetrahydrofuran. After 2 hours, the reaction mixture is treated with 20 ml of 15% sodium hydroxide solution, stirred, and extracted with chloroform. The organic layer is dried and concentrated. The resulting residue is purified by preparative TLC eluting with 10% methanol/chloroform. The resulting oil is dissolved in isopropanol (5 mL) and the solution is treated dropwise with a saturated solution of fumaric acid in methanol until the pH was 3. After 2 hours, crystals are collected of the desired 1-(2-Methoxyphenyl)-4-(2-[6-fluorobenzothiazol-2-ylamino]ethyl)piperazine difumarate (180 mg, m.p. 169–170° C.) as an off white solid. Compound 2, base, $^1$H NMR (CDCl$_3$) 7.45 (m, 1H), 7.25 (m, 1H) , 6.8–7.05 (m, 5H) , 6.18 (bs, 1H), 3.85 (s, 3H), 3.55 (m, 2H), 3.0–3.1 (b, 4H), 2.7 (b, 6H).

EXAMPLE 4

The following compounds are prepared essentially according to the procedures set forth above in Examples 1–3.

(a) 1-(Pyrimidin-2-yl)-4-(2-[benzothiazol-2-yl] aminoethyl)piperazine difumarate (Compound 7, m.p. 161–163° C.).

(b) 1-(Pyrimidin-2-yl)-4-(4-[benzothiazol-2-yl] aminobutyl)piperazine difumarate (Compound 8).

(c) 1-(5-Fluoropyrimidin-2-yl)-4-(2-[benzothiazol-2-yl] aminoethyl) piperazine difumarate (Compound 9, m.p. 174–175° C.).

(d) 1-(5-Methylpyrimidin-2-yl)-4-(2-[benzothiazol-2-yl] aminoethyl) piperazine difumarate (m.p. 167–170° C.)

[alternatively named benzothiazol-2-yl{2-[4-(5-methylpyrimidin-2-yl)piperazinyl]ethyl}amine] (Compound 10).

(e) 1-Phenyl-4-(2-[benzothiazol-2-yl]aminoethyl) piperazine difumarate (m.p. 131–132° C.) [alternatively named benzothiazol-2-yl[2-(4-phenylpiperazinyl)ethyl] amine (Compound 11).

(f) 1-(Pyridin-2-yl)-4-(2-[benzothiazol-2-yl]aminoethyl) piperazine difumarate (m.p. 159–160° C.). [benzothiazol-2-yl[2-(4-(2-pyridyl)piperazinyl)ethyl]amine] (Compound 12).

(g) 1-(4-Chlorophenyl)-4-(2-[benzothiazol-2-yl] aminoethyl)piperazine dihydrochloride (m.p. 230–232° C.). [benzothiazol-2-yl{2-[4-(4-chlorophenyl)piperazinyl] ethyl}amine] (Compound 13).

(h) 1-(4-Fluorophenyl)-4-(2-[benzothiazol-2-yl] aminoethyl)piperazine dihydrochloride (m.p. 229–231° C.). [benzothiazol-2-yl{2-[4-(4-fluorophenyl)piperazinyl] ethyl}amine] (Compound 14).

(i) 1-(2-Methoxyphenyl)-4-(2-[benzothiazol-2-yl] aminoethyl)piperazine difumarate (m.p. 101–103° C.). [benzothiazol-2-yl{2-[4-(2-methoxyphenyl)piperazinyl] ethyl}amine] (Compound 15).

(j) 1-(2-Methoxyphenyl)-4-(3-[benzothiazol-2-yl] aminopropyl) piperazine hydrobromide (m.p. 195–197° C.). [benzothiazol-2-yl{3-[4-(2-methoxyphenyl)piperazinyl] propyl} amine] (Compound 16).

(k) 1-(2-Methoxyphenyl)-4-(2-[4-methoxybenzothiazol-2-yl]aminoethyl)piperazine hydrobromide (Compound 17, m.p. 171–173° C.)

(l) 1-(2-Methoxyphenyl)-4-(2-[4-methylbenzothiazol-2-yl]aminoethyl)piperazine hydrobromide (Compound 18, m.p. 226–227° C.).

(m) 1-(2-Methoxyphenyl)-4-(2-[4-chlorobenzothiazol-2-yl]aminoethyl)piperazine hydrobromide (Compound 19, m.p. 194–195° C.). [(4-chlorobenzothiazol-2-yl){2-[4-(2-methoxyphenyl)piperazinyl]ethyl} amine]

(n) 1-(2-Methoxyphenyl)-4-(2-[6-ethoxybenzothiazol-2-yl]aminoethyl)piperazine hydrobromide (Compound 20, m.p. 227–228° C.).

(o) 1-(2-Methoxyphenyl)-4-(2-[6-methylsulfonylbenzothiazol-2-yl]aminoethyl)piperazine hydrobromide (Compound 21, m.p. 190–196° C.) [2-({2-[4-(2-methoxyphenyl)piperazinyl]ethyl}amino)-6-(methylsulfonyl)benzothiazole]

(p) 1-(Pyrimidin-2-yl)-4-(2-[6-fluorobenzothiazol-2-yl] aminoethyl)piperazine difumarate (Compound 22, m.p. 179–180° C.) [(6-fluorobenzothiazol-2-yl) [2-(4-pyrimidin-2-ylpiperazinyl)ethyl]amine]

(q) 1-(2-Methoxyphenyl)-4-(2-[6-fluorobenzothiazol-2-yl]aminoethyl)piperazine difumarate (Compound 23, m.p. 169–170° C.).

(r) 1-Benzyl-4-(2-[6-fluorobenzothiazol-2-yl] aminoethyl)piperazine difumarate (Compound 24, m.p. 228–229° C.).

(s) 1-(4–Chlorobenzyl)-4-(2-[6-fluorobenzothiazol-2-yl] aminoethyl)piperazine hydrobromide (Compound 25, m.p. 238–240° C.).

(t) 1-(2-Ethoxyphenyl)-4-(2-[6-fluorobenzothiazol-2-yl] aminoethyl)piperazine hydrobromide (Compound 26, m.p. 235–237° C.).

(u) 1-(5-Fluoropyrimidin-2-yl)-4-(2-[6-fluorobenzothiazol-2-yl]aminoethyl)piperazine hydrobromide (Compound 27, m.p. 279–281° C.).

(v) 1-(5-Methylpyrimidin-2-yl)-4-(2-[6-fluorobenzothiazol-2-yl]aminoethyl)piperazine hydrobromide (Compound 28, m.p. 240–250° C.).

(w) 1-(Pyridin-2-yl)-4-(2-[6-fluorobenzothiazol-2-yl] aminoethyl)piperazine hydrobromide (Compound 29, m.p. 259–260° C.).

(x) 1-(3-Trifluoromethylphenyl)-4-(2-[6-fluorobenzothiazol-2-yl]aminoethyl)piperazine hydrobromide (Compound 30, m.p. 259–261° C.).

(y) 1-Phenyl-4-(2-[6-fluorobenzothiazol-2-yl] aminoethyl)piperazine hydrobromide (Compound 31, m.p. 268–270° C.).

(z) 1-(4-Fluorophenyl)-4-(2-[6-fluorobenzothiazol-2-yl] aminoethyl)piperazine hydrobromide (Compound 32, m.p. 270–271° C.).

(aa) 1-(2-Isopropoxyphenyl)-4-(2-[6-fluorobenzothiazol-2-yl]aminoethyl)piperazine hydrobromide (Compound 33, m.p. 216–217° C.) [alternatively named (6-fluorobenzothiazol-2-yl) [2-(4-{[2-(methylethoxy)phenyl]methyl}piperazinyl)ethyl]amine]

(bb) 1-(2-Methoxybenzyl)-4-(2-[6-fluorobenzothiazol-2-yl]aminoethyl)piperazine hydrobromide (Compound 34).

(cc) 1-(2-Isopropoxybenzyl)-4-(2-[6-fluorobenzothiazol-2-yl]aminoethyl)piperazine hydrobromide [(6-fluorobenzothiazol-2-yl) [2-(4-{[2-(methylethoxy)phenyl] methyl}piperazinyl)ethyl]amine] (Compound 35).

(dd) 1-(2-Methoxyphenyl)-4-(2-[6-fluorobenzoxazol-2-yl]aminoethyl)piperazine hydrochloride; [alternatively named (6-fluorobenzoxazol-2-yl) {-2-[4-(2-methoxyphenyl) piperazinyl]ethyl}amine] (Compound 36).

(ee) 1-(Pyrimidin-2-yl)-4-(2-[benzoxazol-2-yl] aminoethyl)piperazine hydrochloride (Compound 37, m.p. 197– 202° C.) [alternatively named benzoxazol-2-yl [2-(4-pyrimidin-2-ylpiperazinyl)ethyl]amine].

(ff) 1-(Pyridin-2-yl)-4-(2-[benzoxazol-2-yl]aminoethyl) piperazine hydrochloride (m.p. 255–265° C.) [alternatively named benzoxazol-2-yl [2-(4-(2-pyridyl)piperazinyl)ethyl] amine (Compound 3).

(gg) 1-(2-Methoxyphenyl)-4-(2-[benzimidazol-2-yl] aminoethyl)piperazine hydrobromide (Compound 38, m.p. 215–216° C.) [benzimidazol-2-yl{2-[4-(2-methoxyphenyl) piperazinyl]ethyl} amine]

(hh) 1-Phenyl-4-(2-[benzimidazol-2-yl]aminoethyl) piperazine hydrobromide (Compound 39, m.p. 241–247° C.).

(ii) 1-(Pyridin-2-yl)-4-(2-[benzimidazol-2-yl]aminoethyl) piperazine hydrobromide (Compound 42, m.p. 290–291° C.).

(jj) 1-(Pyridin-2-yl)-4-(2-[1-ethylbenzimidazol-2-yl] aminoethyl)piperazine hydrobromide; [(1-ethylbenzimidazol-2-yl) [2-(4-(2-pyridyl)piperazinyl)ethyl] amine] (Compound 41). p (kk) 1-(Pyridin-2-yl)-4-(2-[1-isopropylbenzimidazol-2-yl]aminoethyl)piperazine hydrobromide (Compound 42).

(ll) 1-(2-Methoxyphenyl)-4-(2-[1-methylbenzimidazol-2-yl]aminoethyl)piperazine hydrobromide (Compound 43, m.p. 273–274° C.).

(mm) 1-(2-Isopropoxylphenyl)-4-(2-[1-methylbenzimidazol-2-yl]aminoethyl)piperazine hydrobromide (Compound 44, m.p. 285° C., dec).

(nn) 1-(3-Trifluoromethylphenyl)-4-(2-[1-methylbenzimidazol-2-yl]aminoethyl)piperazine hydrobromide (Compound 1, m.p. 283° C., dec) [alternatively named (1-methylbenzimidazol-2-yl) (2-{4-[3-(trifluoromethyl) phenyl]piperazinyl}ethyl)amine].

(oo) 1-(2-Methoxyphenyl)-4-(2-[1-ethylbenzimidazol-2-yl]aminoethyl)piperazine hydrobromide (Compound 45, m.p. 109–110° C.).

(pp) 1-Phenyl-4-(2-[1-ethylbenzimidazol-2-yl]aminoethyl)piperazine hydrobromide (Compound 46, m.p. 270° C., dec).

(qq) 1-Phenyl-4-(2-[1-isopropylbenzimidazol-2-yl]aminoethyl)piperazine hydrobromide (Compound 47).

(rr) benzothiazol-2-yl [2-(4-(2-naphthyl)piperazinyl)ethyl]amine (Compound 4).

EXAMPLE 5

The following salts are prepared essentially according to the procedures set forth above in Examples 1–6 and, where necessary, with reference to literature methods for preparing pharmaceutically acceptable salts.

1-(5-Fluoropyrimidin-2-yl)-4-(2-[6-benzothiazol-2-ylamino]butyl) piperazine (Compound 48).

1-(2-Methoxyphenyl)-4-(2-[6-fluorobenzothiazol-2-ylamino]ethyl) piperazine (Compound 49).

(a) 1-(Pyrimidin-2-yl)-4-(2-[benzothiazol-2-yl]aminoethyl)piperazine (Compound 50).

(b) 1-(Pyrimidin-2-yl)-4-(4-[benzothiazol-2-yl]aminobutyl)piperazine (Compound 51).

(c) 1-(5-Fluoropyrimidin-2-yl)-4-(2-[benzothiazol-2-yl]aminoethyl) piperazine (Compound 52).

(d) 1-(5-Methylpyrimidin-2-yl)-4-(2-[benzothiazol-2-yl]aminoethyl) piperazine (Compound 53).

(e) 1-Phenyl-4-(2-[benzothiazol-2-yl]aminoethyl)piperazine (Compound 54).

(f) 1-(Pyridin-2-yl)-4-(2-[benzothiazol-2-yl]aminoethyl)piperazine (Compound 55).

(g) 1-(4-Chlorophenyl)-4-(2-[benzothiazol-2-yl]aminoethyl)piperazine (Compound 56).

(h) 1-(4-Fluorophenyl)-4-(2-[benzothiazol-2-yl]aminoethyl)piperazine (Compound 57).

(i) 1-(2-Methoxyphenyl)-4-(2-[benzothiazol-2-yl]aminoethyl)piperazine (Compound 58).

(j) 1-(2-Methoxyphenyl)-4-(3-[benzothiazol-2-yl]aminopropyl) piperazine (Compound 59).

(k) 1-(2-Methoxyphenyl)-4-(2-[4-methoxybenzothiazol-2-yl]aminoethyl)piperazine (Compound 60).

(l) 1-(2-Methoxyphenyl)-4-(2-[4-methylbenzothiazol-2-yl]aminoethyl)piperazine (Compound 61).

(m) 1-(2-Methoxyphenyl)-4-(2-[4-chlorobenzothiazol-2-yl]aminoethyl)piperazine (Compound 62).

(n) 1-(2-Methoxyphenyl)-4-(2-[6-ethoxybenzothiazol-2-yl]aminoethyl)piperazine (Compound 63).

(o) 1-(2-Methoxyphenyl)-4-(2-[6-methylsulfonylbenzothiazol-2-yl]aminoethyl)piperazine (Compound 64).

(p) 1-(Pyrimidin-2-yl)-4-(2-[6-fluorobenzothiazol-2-yl]aminoethyl)piperazine (Compound 65).

(q) 1-(2-Methoxyphenyl)-4-(2-[6-fluorobenzothiazol-2-yl]aminoethyl)piperazine (Compound 66).

(r) 1-Benzyl-4-(2-[6-fluorobenzothiazol-2-yl]aminoethyl)piperazine (Compound 67).

(s) 1-(4-Chlorobenzyl)-4-(2-[6-fluorobenzothiazol-2-yl]aminoethyl)piperazine (Compound 68).

(t) 1-(2-Ethoxyphenyl)-4-(2-[6-fluorobenzothiazol-2-yl]aminoethyl)piperazine (Compound 69).

(u) 1-(5-Fluoropyrimidin-2-yl)-4-(2-[6-fluorobenzothiazol-2-yl]aminoethyl)piperazine (Compound 70).

(v) 1-(5-Methylpyrimidin-2-yl)-4-(2-[6-fluorobenzothiazol-2-yl]aminoethyl)piperazine (Compound 71).

(w) 1-(Pyridin-2-yl)-4-(2-[6-fluorobenzothiazol-2-yl]aminoethyl)piperazine (Compound 72).

(x) 1-(3-Trifluoromethylphenyl)-4-(2-[6-fluorobenzothiazol-2-yl]aminoethyl)piperazine (Compound 73).

(y) 1-Phenyl-4-(2-[6-fluorobenzothiazol-2-yl]aminoethyl)piperazine (Compound 74).

(z) 1-(4-Fluorophenyl)-4-(2-[6-fluorobenzothiazol-2-yl]aminoethyl)piperazine (Compound 75).

(aa) 1-(2-Isopropoxyphenyl)-4-(2-[6-fluorobenzothiazol-2-yl]aminoethyl)piperazine (Compound 76).

(bb) 1-(2-Methoxybenzyl)-4-(2-[6-fluorobenzothiazol-2-yl]aminoethyl)piperazine (Compound 77).

(cc) 1-(2-Isopropoxybenzyl)-4-(2-[6-fluorobenzothiazol-2-yl]aminoethyl)piperazine (Compound 78).

(dd) 1-(2-Methoxyphenyl)-4-(2-[6-fluorobenzoxazol-2-yl]aminoethyl)piperazine (Compound 79).

(ee) 1-(Pyrimidin-2-yl)-4-(2-[benzoxazol-2-yl]aminoethyl)piperazine (Compound 80).

(ff) 1-(Pyridin-2-yl)-4-(2-[benzoxazol-2-yl]aminoethyl)piperazine (Compound 81).

(gg) 1-(2-Methoxyphenyl)-4-(2-[benzimidazol-2-yl]aminoethyl)piperazine (Compound 82).

(hh) 1-Phenyl-4-(2-[benzimidazol-2-yl]aminoethyl)piperazine (Compound 83).

(ii) 1-(Pyridin-2-yl)-4-(2-[benzimidazol-2-yl]aminoethyl)piperazine (Compound 84).

(jj) 1-(Pyridin-2-yl)-4-(2-[1-ethylbenzimidazol-2-yl]aminoethyl)piperazine (Compound 85).

(kk) 1-(Pyridin-2-yl)-4-(2-[1-isopropylbenzimidazol-2-yl]aminoethyl)piperazine (Compound 86).

(ll) 1-(2-Methoxyphenyl)-4-(2-[1-methylbenzimidazol-2-yl]aminoethyl)piperazine (Compound 87).

(mm) 1-(2-Isopropoxyphenyl)-4-(2-[1-methylbenzimidazol-2-yl]aminoethyl)piperazine (Compound 88).

(nn) 1-(3-Trifluoromethylphenyl)-4-(2-[1-methylbenzimidazol-2-yl]aminoethyl)piperazine (Compound 89).

(oo) 1-(2-Methoxyphenyl)-4-(2-[1-ethylbenzimidazol-2-yl]aminoethyl)piperazine (Compound 90).

(pp) 1-Phenyl-4-(2-[1-ethylbenzimidazol-2-yl]aminoethyl)piperazine (Compound 91).

(qq) 1-Phenyl-4-(2-[1-isopropylbenzimidazol-2-yl]aminoethyl)piperazine (Compound 92).

EXAMPLE 6

Assays For $D_2$, $D_3$ and $D_4$ Receptor Binding Activity

Pellets of COS cells containing recombinantly produced $D_2$ or $D_4$ receptors from human are used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged again at 30,000×g and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 (Nemonapride, cis-5-Chloro-2-methoxy-4-(methylamino)-N-(2-methyl-2-(phenylmethyl)-3-pyrrolidinyl)benzamide) and the compound of interest in a total incubation of 1.0 ml. Nonspecific binding is defined as that binding found in the presence of 1 mM spiperone; without further additions, nonspecific binding is less than 20% of total binding. The binding characteristics of examples of the invention for $D_2$ and $D_4$ receptor subtypes are shown in Table 2 for rat striatal homogenates.

TABLE 2

| Compound Number | $D_4$ $K_i$ (nM) | $D_2$ $K_i$ (nM) |
| --- | --- | --- |
| 1 | 3 | >10,000 |
| 2 | 1 | 175 |
| 3 | 11 | >10,000 |
| 6 | 6 | 1637 |

The binding constants of compounds of Formula I for the $D_4$ receptor, expressed in nM, generally range from about 0.1 nanomolar (nM) to about 75 nanomolar (nM). Preferably, such compounds have binding constraints of from about 0.1 to 20 nM. These compounds typically have binding constants for the $D_2$ receptor of at least about 100 nM. Thus, the compounds of the invention are generally at least about 10 time more selective for the $D_4$ receptor than the $D_2$ receptor. Preferably, these compounds are at least 20, and more preferably at least 25–50, times more selective for the $D_4$ receptor than the $D_2$ receptor. Most preferably, the compounds of Formula I are at least 500 times more selective for the $D_4$ receptor than the $D_2$ receptor.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

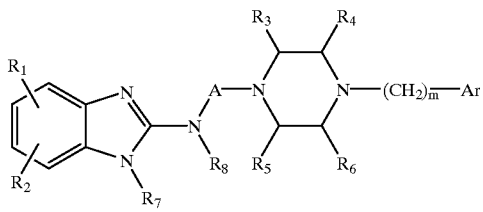

or a pharmaceutically acceptable salt thereof wherein;

A is $C_1$–$C_6$ alkylene optionally substituted with one or two $C_1$–$C_6$ alkyl groups;

$R_1$ and $R_2$ are the same or different and represent hydrogen, halogen, $C_1$–$C_6$ alkyl, $C_1$–$C_6$ alkoxy, $C_1$–$C_6$ alkylthio, hydroxy, amino, mono- or di($C_1$–$C_6$) alkylamino, cyano, nitro, $C_1$–$C_6$ alkylsulfonyl, sulfonamido, perfluoro $C_1$–$C_6$ alkyl or perfluoro $C_1$–$C_6$ alkoxy;

$R_3$, $R_4$, $R_5$, and $R_6$ are the same or different and represent hydrogen or $C_1$–$C_6$ alkyl; and $R_8$ is hydrogen or $C_1$–$C_6$ alkyl;

m is 0, 1 or 2; and

Ar represents phenyl, naphthyl pyrimidinyl, or pyridinyl, each of which is optionally subtituted independently with up to five groups selected from $C_1$–$C_6$ alkyl, $C_1$–$C_6$ alkoxy, halogen, $C_1$–$C_6$ alkylthio, hydroxy, amino, mono- or di($C_1$–$C_6$)alkylamino, cyano, nitro, trifluoromethyl, trifluoromethoxy, $C_1$–$C_6$ alkylsulfonyl, sulfonamido, or N-alkyl sulfonamido.

2. A compound according to claim 1, wherein A is unsubstituted $C_1$–$C_4$ alkylene.

3. A compound according to claim 1 wherein A is $C_2$, $C_3$, or $C_4$ alkylene.

4. A compound according to claim 3 wherein Ar is selected from

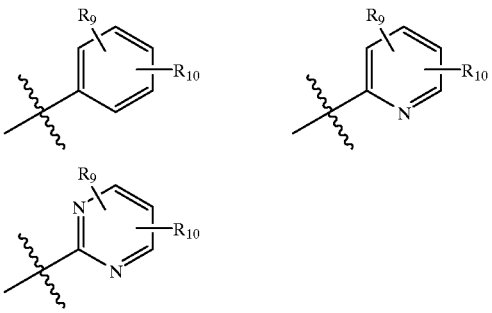

where each of $R_9$ and $R_{10}$ is independently selected from hydrogen, $C_1$–$C_6$ alkyl, $C_1$–$C_6$ alkoxy, halogen, or trifluoromethyl.

5. A compound according to claim 4, wherein $R_9$ and $R_{10}$ are independently selected from hydrogen, $C_1$–$C_3$ alkyl, $C_1$–$C_3$ alkoxy, chloro or fluoro, or trifluoromethyl.

6. A compound according to claim 3 wherein Ar is selected from

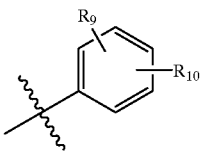

where each of $R_9$ and $R_{10}$ is independently selected from hydrogen, 4-$C_1$–$C_3$ alkyl, 2-$C_1$–$C_3$ alkoxy, 4-halogen, or 3-trifluoromethyl, provided that one of $R_9$ and $R_{10}$ is hydrogen.

7. A compound according to claim 6, wherein $R_9$ and $R_{10}$ are independently selected from hydrogen, methyl, methyoxy, ethoxy, isopropoxy, chloro, or fluoro.

8. A compound according to claim 3, wherein $R_1$ and $R_2$ independently represent hydrogen, halogen, $C_1$–$C_6$ alkoxy, $C_1$–$C_6$ alkyl, $C_1$–$C_6$ alkylsulfonyl, sulfonamido, or N-alkyl sulfonamido.

9. A compound according to claim 8, wherein at least one of $R_1$ and $R_2$ is hydrogen and the other is methoxy, methyl, chloro, fluoro, methoxy, ethoxy, or methylsulfonyl.

10. A compound according to claim 9, wherein $R_1$ is hydrogen and $R_2$ is in the 4 or 6 position on the nitrogen containing ring system.

11. A compound according to claim 3, wherein Ar is

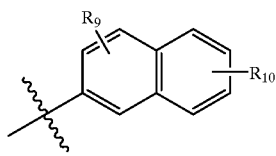

where each of $R_9$ and $R_{10}$ is independently selected from hydrogen, $C_1$–$C_6$ alkyl, $C_1$–$C_6$ alkoxy, halogen, or trifluoromethyl.

12. A compound according to claim 11, wherein $R_1$ is hydrogen.

13. A compound according to claim 1, which has the formula:

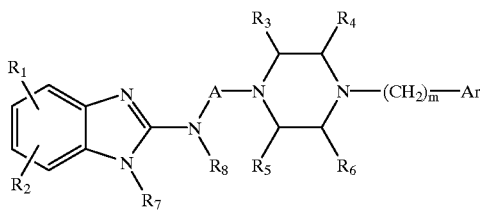

wherein:
A is $C_1$–$C_6$ alkylene;
$R_1$ and $R_2$ are the same or different and represent hydrogen, halogen, $C_1$–$C_6$ alkyl, $C_1$–$C_4$ alkoxy, $C_1$–$C_6$ alkylthio, hydroxy, amino, mono- or di($C_1$–$C_6$) alkylamino, cyano, nitro, $C_1$–$C_6$ alkylsulfonyl, sulfonamido, trifluoromethyl or trifluoromethoxy;
$R_3$, $R_4$, $R_5$, and $R_6$ are the same or different and represent hydrogen or methyl;
$R_7$ is hydrogen or $C_1$–$C_6$ alkyl; and
$R_8$ is hydrogen or $C_1$–$C_6$ alkyl;
m is 0, 1 or 2; and
Ar represents phenyl, pyrimidinyl, or pyridinyl, each of which is optionally substituted independently with up to five groups selected from $C_1$–$C_6$ alkyl, $C_1$–$C_6$ alkoxy, halogen, $C_1$–$C_6$ alkylthio, hydroxy, amino, mono- or di($C_1$–$C_6$)alkylamino, cyano, nitro, trifluoromethyl, trifluoromethoxy, $C_1$–$C_6$ alkylsulfonyl, sulfonamido, or N-alkyl sulfonamido.

14. A compound according to claim 1 which is
1-(2-Methoxyphenyl)-4-(2-[benzimidazol-2-yl]aminoethyl)piperazine;
1-Phenyl-4-(2-[benzimidazol-2-yl]aminoethyl)piperazine;
1-(Pyridin-2-yl)-4-(2-[benzimidazol-2-yl]aminoethyl)piperazine;
1-(Pyridin-2-yl)-4-(2-[1-ethylbenzimidazol-2-yl]aminoethyl)piperazine;
1-(Pyridin-2-yl)-4-(2-[1-isopropylbenzimidazol-2-yl]aminoethyl)piperazine;
1-(2-Methoxyphenyl)-4-(2-[1-methylbenzimidazol-2-yl]aminoethyl)piperazine;
1-(2-Isopropoxylphenyl)-4-(2-[1-methylbenzimidazol-2-yl]aminoethyl)piperazine;
1-(3-Trifluoromethylphenyl)-4-(2-[1-methylbenzimidazol-2-yl]aminoethyl)piperazine;
1-(2-Methoxyphenyl)-4-(2-[1-ethylbenzimidazol-2-yl]aminoethyl)piperazine;
1-Phenyl-4-(2-[1-ethylbenzimidazol-2-yl]aminoethyl)piperazine; or
1-Phenyl-4-(2-[1-isopropylbenzimidazol-2-yl]aminoethyl)piperazine.

15. A salt according to claim 1 which is
1-(3-Trifluoromethylphenyl)-4-(2-[1-methylbenzimidazol-2-yl]aminoethyl)piperazine hydrobromide;
1-(2-Methoxyphenyl)-4-(2-[1-ethylbenzimidazol-2-yl]aminoethyl)piperazine hydrobromide;
1-Phenyl-4-(2-[1-ethylbenzimidazol-2-yl]aminoethyl)piperazine hydrobromide;
1-Phenyl-4-(2-[1-isopropylbenzimidazol-2-yl]aminoethyl)piperazine hydrobromide.

16. A salt according to claim 1 which is
1-(2-Methoxyphenyl)-4-(2-[benzimidazol-2-yl]aminoethyl) piperazine hydrobromide;
1-Phenyl-4-(2-[benzimidazol-2-yl]aminoethyl)piperazine hydrobromide;
1-(Pyridin-2-yl)-4-(2-[benzimidazol-2-yl]aminoethyl)piperazine hydrobromide;
1-(Pyridin-2-yl)-4-(2-[1-ethylbenzimidazol-2-yl]aminoethyl)piperazine hydrobromide;
1-(Pyridin-2-yl)-4-(2-[1-isopropylbenzimidazol-2-yl]aminoethyl)piperazine hydrobromide;
1-(2-Methoxyphenyl)-4-(2-[1-methylbenzimidazol-2-yl]aminoethyl)piperazine hydrobromide; or
1-(2-Isopropoxylphenyl)-4-(2-[1-methylbenzimidazol-2-yl]aminoethyl) piperazine hydrobromide.

17. A method for the treatment of schizophrenia, which comprises administering to a host in need of such treatment an effective amount of a compound as claimed in claim 1.

18. A method for the treatment of Parkinson-like motor disorders which comprises administering to a host in need of such treatment an effective amount of a compound as claimed in claim 1.

19. A pharmaceutical composition comprising a compound or salt according to claim 1 together with at least one pharmaceutically acceptable carrier.

* * * * *